United States Patent
Kleinworth et al.

(10) Patent No.: US 7,244,873 B1
(45) Date of Patent: Jul. 17, 2007

(54) PROCESS AND APPARATUS FOR SEPARATING OXYGENATE MODIFIER FROM OLIGOMERIZATION EFFLUENT BY WATER WASH

(75) Inventors: Ruth Buskus Kleinworth, Winfield, IL (US); Charles P. Luebke, Mount Prospect, IL (US)

(73) Assignee: UOP LLC, Des Plaines, IL (US)

( * ) Notice: Subject to any disclaimer, the term of this patent is extended or adjusted under 35 U.S.C. 154(b) by 885 days.

(21) Appl. No.: 10/125,630

(22) Filed: Apr. 18, 2002

(51) Int. Cl.
*C07C 7/08* (2006.01)
(52) U.S. Cl. .............. 585/809; 585/502; 585/510; 585/511; 208/311; 208/313; 208/323
(58) Field of Classification Search .............. 585/809, 585/502, 510, 511; 208/311, 313, 323
See application file for complete search history.

(56) References Cited

U.S. PATENT DOCUMENTS

| 4,313,016 A | 1/1982 | Manning | 585/832 |
|---|---|---|---|
| 4,447,668 A * | 5/1984 | Smith et al. | 585/639 |
| 4,956,513 A | 9/1990 | Walker et al. | 585/525 |
| 5,146,032 A | 9/1992 | Harandi | 585/640 |
| 6,590,132 B1 * | 7/2003 | Vora | 585/809 |

FOREIGN PATENT DOCUMENTS

EP   0 994 088 A1   4/2000

OTHER PUBLICATIONS

Article "Consider New Technologies to Replace MTBE" by M.J. Tsai et al., *Hydrocarbon Processing*, Feb. 2002, pp. 81-87.

\* cited by examiner

*Primary Examiner*—Tam M. Nguyen
(74) *Attorney, Agent, or Firm*—James C Paschall

(57) ABSTRACT

It has now been disclosed that by directing the effluent from an oligomerization reactor to a water wash column to remove alcohol modifier from the hydrocarbon stream before sending it to a fractionation column offers flexibility in providing a bottoms product of a desired vapor pressure without increasing the concentration of alcohol modifier in the overhead stream beyond alcohol concentration limits.

7 Claims, 1 Drawing Sheet

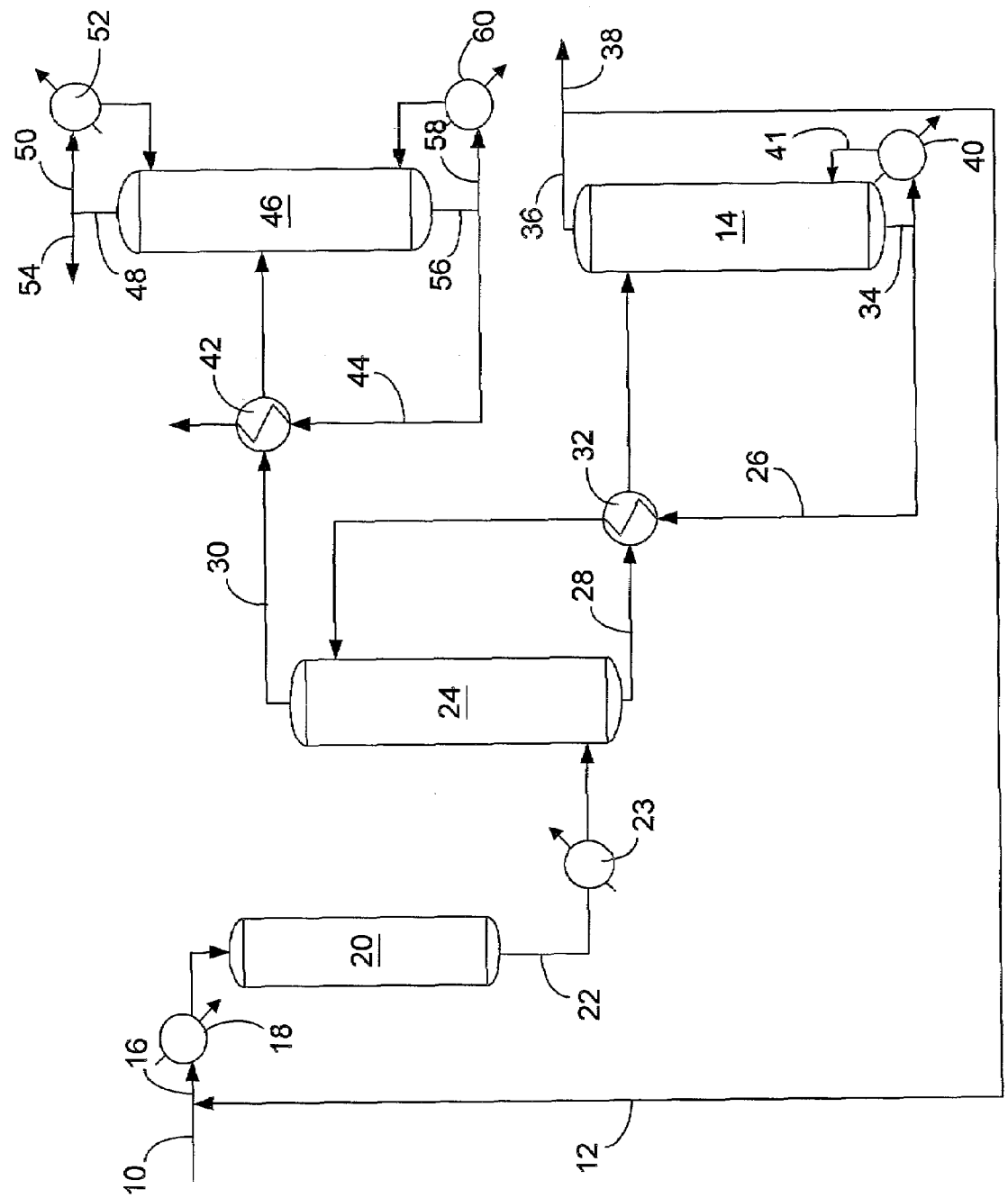

US 7,244,873 B1

PROCESS AND APPARATUS FOR SEPARATING OXYGENATE MODIFIER FROM OLIGOMERIZATION EFFLUENT BY WATER WASH

FIELD OF THE INVENTION

This invention relates to a process and apparatus for separating oxygenate modifiers from product oligomerized hydrocarbons. Specifically, alcoholic modifiers are separated from oligomerized hydrocarbons by a water wash column.

BACKGROUND OF THE INVENTION

Processes for the oligomerization of light olefins to produce $C_8$ olefin oligomers are known. Oligomerization processes have been long employed to produce high quality motor fuel from $C_4$ olefins. Such oligomerization processes are also referred to as catalytic condensation and polymerization with the resulting motor fuel often referred to as polymer gasoline. Methods have always been sought to improve the octane number of the gasoline boiling range oligomerization products. Indirect alkylation is a noteworthy $C_4$ olefin dimerization process.

In one form of the indirect alkylation process, an ionic exchange resin catalyst oligomerizes light olefins to produce oligomers such as $C_8$ olefins. In such processes, the oligomerization zone can be preceded by a dehydrogenation zone to convert paraffinic feed into olefinic feed and/or succeeded by a hydrogenation zone to convert heavy oligomeric olefins into heavy alkanes that can be blended with gasoline stock.

U.S. Pat. No. 4,313,016 B1 discloses a heat exchanged oligomerization reactor that contains a cationic exchange resin catalyst $C_4$ olefins contacted with the resin catalyst oligomerize to $C_4$ oligomers. Water or methanol may be present in small amounts insufficient to form an entrained second phase to serve as a catalyst modifier.

Modern oligomerization processes often include an oxygenate such as tert-butyl alcohol (TBA) and/or sec-butyl alcohol (SBA) in the feed for modifying the catalyst to maintain desired product selectivity. The modifier does not participate in the reaction. References disclosing resin catalyzed oligomerization in the presence of an oxygenate modifier include U.S. Pat. No. 5,877,372 B1 and EP 994 088 A1. TBA and SBA have become the resin catalyst modifier of preference.

More recently, higher quantities of alcohol modifier have been used in resin catalyzed oligomerizations. Consequently, removing the alcohol modifier from the hydrocarbon oligomerization product stream has become more important. In such oligomerization processes, it is typically necessary to separate unreacted light olefins from the product heavy oligomers in the effluent from the oligomerization zone. Separation is conventionally performed in a distillation column typically following the oligomerization zone. The lighter components comprising primarily unreacted $C_4^-$ olefins and compounds that were present in the feed stream exit from the overhead of the distillation column. The heavier components comprising primarily heavy oligomers such as $C_5^+$ olefins and compounds exit out the bottoms of the distillation column. If the distillation column is operated to send all of the $C_5^+$ material contained in the oligomerization effluent to the bottoms, most of the alcohol modifier would exit with the bottoms product and only a small amount of alcohol modifier would exit in the overhead stream. A water wash column was designed to treat the bottoms product and recover the alcohol modifier before the $C_5^+$ stream proceeded to product storage or further treatment.

Reid vapor pressure is a standard unit used in governmental specifications regarding gasoline product vapor pressures. To meet increasingly tight governmental specifications, the distillation column must be operated so as to control the vapor pressure of the bottoms product. In this case, some of the $C_5$ compounds are diverted from the bottoms to the overhead product. Consequently, a portion of the alcohol modifier will azeotrope with the $C_5$ material and both the overhead and bottoms stream will contain alcohol modifier. As such, alcohol modifier must be removed from both the overhead and the bottoms product streams.

U.S. Pat. No. 4,956,513 B1 discloses an oligomerization process that uses a homogeneous boron trifluoride catalyst with a promoter such as normal butanol. After the oligomerization, the boron trifluoride catalyst is extracted from the reactor effluent by water washing. The water extract containing the major part of the boron trifluoride catalyst is then distilled to remove the water in the promoter.

U.S. Pat. No. 5,146,032 B1 discloses reacting $C_3^+$ olefins with methanol over a ZSM-5 catalyst to produce a range of hydrocarbons including an olefinic gasoline stream. The unreacted methanol and water present are separated by cooling, phase separation and, in some cases, by water washing of the hydrocarbon effluent leaving the reactor. They are then led to a methanol-water separator such as a distillation tower.

An object of the present invention is to fractionate oligomerization effluent to provide a heavy oligomer bottoms product with a desired vapor pressure and a light olefin overhead stream with a sufficiently low concentration of alcohol modifier.

An additional object of the present invention is to fractionate oligomerization effluent without having to utilize a separate water wash column on both the heavy oligomer bottoms product and the light olefin overhead streams

SUMMARY OF THE INVENTION

It has now been discovered that by directing an effluent from an oligomerization reactor to a water wash column to remove alcohol modifier from the hydrocarbon stream before sending it to a fractionation column offers flexibility in providing a bottoms product of a desired vapor pressure without increasing the concentration of alcohol modifier in the overhead stream beyond alcohol concentration limits. The present invention recognizes the heretofore unknown problem that if greater quantities of $C_5$ hydrocarbons are allowed to go up in the overhead to adjust the vapor pressure of the bottoms product of the fractionation column, too much alcohol modifier goes with the $C_5$ hydrocarbons out with the overhead stream. Hence, it was difficult to provide a bottoms product that comprises olefinic gasoline that can meet the vapor pressure specification and, at the same time, provide an overhead product comprising mainly unreacted $C_4$ hydrocarbons that can meet the alcohol specification. The present invention solves the discovered problem by inserting a water wash column prior to the fractionation column instead of having to separately water wash each of the overhead stream and the bottoms stream from the fractionation column. The water wash column adequately removes all but trace quantities of alcohol modifier from the hydrocarbon stream which can then be fractionated in the distillation column at the desired cut between $C_4$ hydrocarbons and $C_5$ hydrocarbons to meet specifications in both the overhead and bottoms streams.

Accordingly, in one embodiment, the present invention relates to a process for oligomerizing light olefins and recovering heavy olefins comprising feeding a reactant stream of light olefins and a non-reactant stream of alcohol modifier with at least three carbons to a reactor containing a solid resin catalyst; catalytically oligomerizing the light olefins to heavy olefins in the reactor; passing a reactor effluent stream comprising heavy olefins, unreacted light olefins and alcohol modifier to a water wash column; washing the reactor effluent stream with water in the water wash column; withdrawing a wash effluent hydrocarbon stream comprising heavy olefins and unreacted light olefins from the water wash column; withdrawing an extract stream comprising water and alcohol modifier from the water wash column; passing the wash effluent hydrocarbon stream to a separation column; separating the light olefins from the heavy olefins; and recovering heavy olefins from the separation column.

In another embodiment, the present invention relates to an apparatus for oligomerizing light olefins and recovering heavy olefins comprising an oligomerization reactor vessel including a feed inlet for delivering light olefins to the reactor vessel and a product outlet for removing light olefins and heavy olefins from the reactor vessel; a water wash column including a hydrocarbon inlet in communication with the product outlet of the reactor vessel, a water inlet near a top thereof, a water outlet near a bottom thereof and a hydrocarbon outlet near a top thereof; and a separation column including a hydrocarbon feed inlet in communication with the hydrocarbon outlet of the water wash column, a light olefin outlet near a top thereof and a heavy olefin outlet near a bottom thereof.

In a further embodiment, the present invention relates to an apparatus for oligomerizing light olefins and recovering heavy olefins comprising an oligomerization reactor vessel including a feed inlet for delivering light olefins to the reactor vessel and a product outlet for removing light olefins and heavy olefins from the reactor vessel; a water wash column including a hydrocarbon inlet in communication with the product outlet of the reactor vessel, a water inlet near a top thereof, a water outlet near a bottom thereof and a hydrocarbon outlet near a top thereof; a separation column including a hydrocarbon feed inlet in communication with the hydrocarbon outlet of the water wash column, a light olefin outlet near a top thereof and a heavy olefin outlet near a bottom thereof; and a stripper column having an inlet in communication with the water outlet of the water wash column, the stripper column having a water outlet in communication with the water inlet of the water wash column for recycling water from the stripper column to the water wash column.

Additional objects, embodiments and details of this invention can be obtained from the following detailed description of the invention.

BRIEF DESCRIPTION OF THE DRAWING

The FIGURE illustrates a flow scheme for the distillative separation of the present invention.

DETAILED DESCRIPTION OF THE INVENTION

The present invention provides for directing effluent from an oligomerization reactor containing unreacted light hydrocarbons, heavy product hydrocarbons and oxygenate modifier to a water wash column to remove the oxygenate modifier from the hydrocarbons. The oxygenate modifier is preferably an alcohol. The water washed hydrocarbon free of all but trace quantities of alcohol modifier are then fractionated in a distillation column. Hence, the split between light hydrocarbons and heavy hydrocarbons in the distillation column can be adjusted to obtain desired properties without having to water wash both the overhead and bottoms streams from the fractionation column separately. The extracted water/modifier stream is then stripped to separate the water and the alcohol modifier. Both separated components are then recycled back to the process.

Preferred catalyst for the oligomerization reaction can generally be described as protonic acids. The preferred acids will generally have a Hammett acidity function of –4.0 or less. Examples of catalysts falling into this category include phosphoric acid catalysts. Solid phosphoric acid catalyst has a Hammett acidity function of approximately –5.0 or lower. A particularly preferred catalyst is a sulfonic acid ion-exchange resin catalyst. This resin catalyst comprises sulfonic acid groups and can be prepared by polymerizing or copolymerizing aromatic vinyl compounds followed by sulfonating. Examples of aromatic vinyl compounds include the following: styrene, vinyl toluene, vinyl naphthalene, vinyl ethylbenzene, methyl styrene, vinyl chlorobenzene and vinyl xylene. An acidic ion-exchange resin contains typically approximately 1.3 to 2.0 sulfonic acid groups per aromatic group. Preferred resins are those based on copolymers of aromatic monovinyl compounds and aromatic polyvinyl compounds and in particular divinyl compounds in which the concentration of polyvinyl benzene is approximately 1 to 20 wt-% of the copolymer. The particle size of the ion-exchange resin is preferably approximately 0.15 to 1 mm. Furthermore, perfluorosulfonic acid resins consisting of copolymers of sulphonylfluorovinyl ethyl and fluorocarbon compounds can be used. Various suitable ion-exchange resins are commercially available under the name, for example, Amberlyst 15. The concentration of the catalyst is typically 0.01 to 20% of the mixture it is catalyzing and preferably 0.1 to 10% of the weight thereof.

The feed for the oligomerization reactor will typically be a $C_4$ cut from a debutanizing distillation column that follows a fluidized catalytic cracking (FCC) unit. The feed will typically comprise $C_3$ to $C_5$ aliphatic olefins A non-reactive, water-soluble oxygenate modifier such as an alcohol with at least three carbons and preferably tert-butyl alcohol (TBA) and/or sec-butyl alcohol (SBA) is also added to the oligomerization reactor to attenuate the resin catalyst but not to participate in the reaction. TBA is also generated in the reaction zone when isobutene reacts with water over a resin catalyst. Similarly, SBA is generated from a reaction of water and normal butene. Additionally, other alcohols will form when other olefins, such as C3 and C5 olefins in the feed encounter water in the presence of the resin catalyst. Moreover, olefins and alcoholic modifier react over resin catalyst to generate ethers.

Oligomerization reaction zones in general are maintained at conditions that may vary widely. The temperature of the oligomerization reaction zone in which a resin catalyst is used is typically 0° to 250° C. (320 to 482° F.) and preferably 40° to 150° C. (104° to 302° F.). Pressures in the oligomerization zone using the resin catalyst will be sufficient to maintain the liquid phase, typically 345 to 3447 kPa (50 to 500 psig), and preferably 1380 to 2413 kPa (200 to 350 psig). Oligomerization conditions may also include a liquid hourly space velocity (LHSV) of 0.5 to 8 hr$^{-1}$ with 1 to 6 hr$^{-1}$ being preferred.

The water wash or extractor column operates at temperatures of 24 to 52° C. (75 to 150° F.) and pressures of 552 to 827 kPa (80 to 120 psia). The mass ratio of water to hydrocarbon is between 0.25 and 1.0 and preferably between 0.6 and 0.9. Water is delivered to the column near the top and hydrocarbon and modifier feed are delivered near the bottom of the column. Hydrocarbons including ethers leave the top of the column, substantially free of alcohol modifier and an extract stream of water and alcohol modifier leave the bottom of the column. In addition to TBA and SBA, substantially all of the alcohols formed in the reaction zone will exit in the extract stream. The water wash column preferably has a series of trays for enhancing the contact between the water and the modifier containing hydrocarbon stream.

A debutanizing distillation fractionation column usually runs at pressures of between 413 and 1034 kPa (60 and 150 psig) and preferably between 517 and 827 kPa (75 and 120 psig). To make the separation between $C_4$ and $C_5$ hydrocarbons at those pressures, the bottoms temperature will have to be around 149 to 204° C. (300 to 400° F.) and the overhead temperature will have to be around 38 to 66° C. (100 and 150° F.) to obtain the appropriate separation.

Any suitable reflux ratio can be employed in the distillation column. The reflux ratio is the weight ratio of the portion of condensed vapor which is returned to the distillation column to the portion of condensed vapor which is withdrawn as distillate product. Generally, the reflux ratio is in the range of from about 0.1:1 to about 2:1, and preferably in the range of from about 0.5:1 to about 1.3:1.

Any suitable feed entry location to the fractionation column can be selected. Generally, the feed entry location is in the range of from about 2 to about 70 percent of the total height of the column, measured upward from the bottom of the column. Preferably, in the context of the present invention, the feed entry location is in the range of from about 20 to about 60 percent and more preferably in the range of from about 25 to about 50 percent of the total column height.

The overhead distillate product withdrawn from the top of the column generally contains a larger volume percentage of the light hydrocarbons than the feed and a smaller volume percentage of the heavy hydrocarbons than the feed. The overhead product will predominately comprise unreacted light olefins, e.g., $C_4$ olefins. A portion of the overhead product may be cooled and recycled to the higher portion of the column. Generally, the bottoms product contains a larger volume percentage of heavy components than the feed, and less of the light components than the feed. A portion of the bottoms product may be reheated and recycled to the lower portion of the column. Any suitable total column height and column diameter and number of trays in the distillation column may be employed. The exact dimensions and column designs depend on the scale of the operation, the exact feed composition, the desired recovery and degree of purity of the product, and the like, and can be determined by those having ordinary skill in the art.

Water washing the entire effluent from the oligomerization reactor will require feeding substantially more water to the water wash column. Hence, it may be desirable to arrange the piping of the apparatus to accommodate selectively sending the oligomerization effluent either to the water wash column directly or to the fractionation column directly. In the latter case, the bottoms product would then be sent to the water wash column if circumstances would permit only water washing the bottoms product.

The invention is disclosed with reference to the FIGURE which shows an oligomerization scheme which uses a resin catalyst in the oligomerization reactor. However, other oligomerization reaction processes can be used in accordance with the present invention.

Feed comprising a $C_4$ hydrocarbon stream from an FCC debutanizer fractionation column that may have previously been water washed to remove nitrites and trace amines and statically mixed, which processes are both not shown, is brought into the process via a feed line 10. The $C_4$ hydrocarbon stream typically predominantly includes mixed butenes, mixed butanes and also may include lower alkanes and olefins and $C_5$ hydrocarbons. A modifier stream comprising an oxygenate such as an alcohol and preferably tert-butyl alcohol (TBA) and/or sec-butyl alcohol (SBA) in an azeotropic mixture with water are added to the feed line 10 via a modifier line 12 from a stripper column 14. The alcohol and water from the modifier line 12 are combined with the feed from the feed line 10 to form a combined line 16. The combined line 16 is heated by a heater 18 and enters an oligomerization reactor 20. Alternatively, the modifier line 12 and the feed line 10 enter the oligomerization reactor 20 separately. In the oligomerization reactor 20, the feed contacts a solid acid catalyst, preferably a resin catalyst under oligomerization conditions. The light olefins in the feed which are preferably predominantly $C_4$ olefins oligomerize to heavy oligomers which are preferably predominantly $C_8$ olefins. The oligomerization effluent comprising unreacted light olefins, heavy product oligomers, alcohol modifier and water is carried via a line 22 through a cooler 23 to a water wash column 24.

In the water wash column 24, a liquid—liquid extraction occurs in which water extracts the water-soluble, alcoholic, modifier from the water-insoluble hydrocarbons comprising ethers, unreacted light olefins and heavy product oligomers. Water is added near the top of the water wash column 24 from a water line 26. The water/modifier stream exits the bottom of the water wash column 24 via an extract line 28 whereas the hydrocarbons go out the overhead of the water wash column 24 via a hydrocarbon line 30. The extract line 28 carries the water/modifier mixture to a heat exchanger 32 which exchanges heat with the water line 26 to heat the water line 26. The cooled extract line 28 then enters the stripper column 14. In the stripper column 14, the water is separated from the alcohol modifier. Water exits the bottom of the stripper column 14 through a water line 34 which splits into two portions. A first portion is recycled back to the water wash column 24 by the water line 26. The second portion is heated in a reboiler 40 and returned to the stripper column 14 through a return line 41. The water/alcohol azeotrope is brought out the overhead via an overhead line 36. A portion of the water/alcohol stream in the overhead line 36 is recycled back by the alcohol modifier line 12 to the influent for the oligomerization reactor 20. Another portion of the stream in the overhead line 36 is transported to further processing by a line 38.

The hydrocarbon stream in the hydrocarbon line 30 from the water wash column 24 is heated indirectly by an oligomer product line 44 in a heat exchanger 42. The heated hydrocarbons in the hydrocarbon line 30 are then delivered to a debutanizer fractionation column 46. The hydrocarbons in the hydrocarbon line 30 contain no more than trace amounts of alcohol modifier. The split in the fractionation column 46 is effected between the $C_4$ and the $C_5$ hydrocarbons. However, as much $C_5$ hydrocarbons can be sent to the overhead as necessary to lower the vapor pressure of the bottoms without concern that too much alcohol modifier will be present in the overhead stream. An overhead line 48 comprising predominantly $C_4$ hydrocarbons, very little $C_5$ hydrocarbons and no more than trace quantities of alcohol is split into two portions. A first portion in a reflux line 50 is cooled in a condenser 52 and refluxed back to the fractionation column 46. The other portion of the overhead line 48 is carried to further processing by a line 54 which may include either a direct alkylation unit or preparation for entry into a dehydrogenation unit for further indirect alkylation processing. A bottoms stream comprising $C_5^+$ hydrocarbons, a predominant amount of $C_8$ olefin oligomers and substantially all of the ethers in a bottoms line 56 is split into a first portion which is carried by the oligomer product line 44 for indirect cooling by heat exchange with the hydrocarbon line 30 in the heat exchanger 42. The cooled oligomer product in the oligomer product line 44 then proceeds to further processing or storage. A second portion of the bottoms line 56 is carried by a reboil line 58 to a reboiler 60 where it is heated and is recirculated back to the fractionation column 46.

EXAMPLE

We compared the process of directly fractionating the effluent from an oligomerization zone to water washing the effluent from an oligomerization zone before fractionation by simulation. The oligomerization zone predominantly dimerizes $C_4$ olefins to $C_8$ olefins over a resin catalyst modified by TBA and SBA. In the fractionation column, the primary split is between $C_4$ and lighter hydrocarbons and $C_5$ and heavier hydrocarbons. At the operating specification that requires the bottoms oligomerization product to have a vapor pressure of 41 kPa (6 psi) or less, the split between $C_4^-$ hydrocarbons and $C_5^+$ hydrocarbons would require at least 40% of the $C_5$ hydrocarbons to be distilled to the overhead. Unfortunately, under these conditions, the concentration of TBA/SBA modifier that is carried with the $C_5$ hydrocarbons to the overhead stream exceeds 1,000 ppm which is much higher than the typical 5 ppm alcohol limits required of the overhead stream. In fact, to meet a 5 ppm alcohol limits for the overhead, the Reid Vapor Pressure in the bottoms would have to be as high as 255 kPa (37 psi). Accordingly, to reduce the TBA/SBA modifier in the overhead stream to be within limits and to keep the Reid Vapor Pressure of the bottoms product within the Reid Vapor Pressure limits, both the overhead stream and the bottoms stream would need to be water washed.

According to the present invention, the effluent from the oligomerization reactor is water washed to remove the TBA/SBA modifier from the oligomerization effluent stream and then the hydrocarbon effluent stream free of TBA/SBA modifier is sent to a debutanizer distillation column. The water wash column runs with a ratio of water to hydrocarbon of 0.75, a water wash inlet temperature of 38° C. (100° F.), a hydrocarbon feed temperature of 58° C. (136° F.) and a column pressure of about 690 kPa (100 psi). The water extracts practically all of the TBA/SBA modifier from the hydrocarbon feed. Hence, the hydrocarbon feed is then run to a debutanizer distillation column. To meet the Reid vapor pressure operating specification of 41 kPa (6 psi) in the oligomerization bottoms product of the debutanizing distillation column, over 40% of the $C_5$ hydrocarbons must be sent to the overhead. However, the concentration of alcoholic modifier in the overhead stream is less than 0.4 ppm. Hence, placing the water wash column before the fractionation column allows the vapor pressure specification in the bottom product and the alcohol specification in the overhead stream to be met.

What is claimed is:

1. A process for oligomerizing light olefins and recovering heavy olefins comprising:
    a) feeding a reactant stream of light olefins and a non-reactant stream of alcohol modifier with at least three carbons to a reactor containing a solid resin catalyst;
    b) catalytically oligomerizing said light olefins to heavy olefins in said reactor;
    c) passing a reactor effluent stream comprising heavy olefins, unreacted light olefins and alcohol modifier to a water wash column;
    d) washing said reactor effluent stream with water in said water wash column;
    e) withdrawing a wash effluent hydrocarbon stream comprising heavy olefins and unreacted light olefins from said water wash column;
    f) withdrawing an extract stream comprising water and alcohol modifier from said water wash column;
    g) passing said wash effluent hydrocarbon stream to a separation column;
    h) separating said light olefins from said heavy olefins; and
    i) recovering heavy olefins from said separation column.

2. The process of claim 1 wherein water is added near a top of said water wash column.

3. The process of claim 1 further comprising feeding said extract stream to a stripper column.

4. The process of claim 3 further comprising withdrawing an alcohol modifier stream from near a top of said stripper column, at least part of said alcohol modifier stream comprising said non-reactant stream fed to said reactor.

5. The process of claim 3 further comprising withdrawing a water stream from near a bottom of said stripper column and recycling at least a part of said water stream to said water wash column.

6. The process of claim 1 further comprising recovering light olefins from said separation column.

7. The process of claim 1 wherein a cut between said light olefins and said heavy olefins in said separation column is between $C_4$ hydrocarbons and $C_5$ hydrocarbons.

* * * * *